(12) United States Patent
Richards et al.

(10) Patent No.: US 7,720,701 B2
(45) Date of Patent: May 18, 2010

(54) AUTOMATED CONFIGURATION OF MEDICAL PRACTICE MANAGEMENT SYSTEMS

(75) Inventors: Brady Richards, Allston, MA (US); Laurie Mullin, Reading, MA (US)

(73) Assignee: athenahealth, Inc., Watertown, MA (US)

( * ) Notice: Subject to any disclaimer, the term of this patent is extended or adjusted under 35 U.S.C. 154(b) by 0 days.

(21) Appl. No.: 12/509,579

(22) Filed: Jul. 27, 2009

(65) Prior Publication Data
US 2009/0281831 A1    Nov. 12, 2009

Related U.S. Application Data

(63) Continuation of application No. 12/408,561, filed on Mar. 20, 2009, which is a continuation of application No. 11/779,926, filed on Jul. 19, 2007.

(60) Provisional application No. 60/832,073, filed on Jul. 20, 2006.

(51) Int. Cl.
*G06Q 40/00* (2006.01)

(52) U.S. Cl. .................. 705/4; 705/2; 705/3; 705/40; 707/102; 709/219

(58) Field of Classification Search ............ 395/200; 707/1, 10, 102; 705/2–4; 709/219
See application file for complete search history.

(56) References Cited

U.S. PATENT DOCUMENTS

| | | | |
|---|---|---|---|
| 5,890,129 A * | 3/1999 | Spurgeon | ............... 705/4 |
| 7,343,364 B2 | 3/2008 | Bram et al. | |
| 2002/0133503 A1 | 9/2002 | Amar et al. | |

* cited by examiner

*Primary Examiner*—Gerald J. O'Connor
*Assistant Examiner*—Linh-Giang Michelle Le
(74) *Attorney, Agent, or Firm*—Proskauer Rose LLP

(57) ABSTRACT

A user (e.g., medical office manager, medical office insurance administrator, doctor) utilizes a medical practice configuration interface (e.g., web page) to input information about the user's medical practice (e.g., address, insurance plans, doctors, hospitals that the doctors utilize). Based on this information and/or rules associated with the insurance plans accepted at the user's medical practice, additional information is requested from the user about the user's medical practice (e.g., information needed for an insurance plan, information needed for a hospital). The user inputs the requested additional information utilizing the medical practice configuration interface. Configuration information for the user's medical practice is generated based on the information and/or the additional information inputted by the user. A user interface (e.g., web pages interfacing with the medical practice management server) and/or rules for the medical practice can be generated based on the configuration information.

10 Claims, 31 Drawing Sheets

FIG. 4A athenaImplementation Wizard v8.5 MA-Briarpatch Pediatrics [ not live ] - Microsoft Internet Explorer messages | go to athenaNet | logout

| home | practice | payors | patients | operations | financials | training | table of contents | medical groups | departments | providers | chapter review

Setting up your Medical Group(s)

A medical group is the entity that receives payments from patients and payors. Your practice may have more than one medical group, depending on how it is structured. However, most small groups have only one.

*For example:*

ABC Medical Group has two physicians, Jane Doe and John Smith. Insurance companies issue payment for both physicians to ABC Medical Group, Inc. As there is one financial entity, there is one medical group.

XYZ Medical Associates has two physicians, Sally Smart and Jack Jones. While both physicians share the same staff and office space, insurance companies issue payment for each physician separately. Checks for Dr. Smart are made to Sally Smart, M.D., P.C.; checks for Dr. Jones are made to Jack Jones, M.D., LLC. As there are two financial entities, there are two medical groups.

[CMS 1500] On the CMS-1500 claim form, the medical group information appears in Box 33. Medical group information also appears on patient forms printed from athenaNet, such as patient receipts and encounter forms.

Page 0

Practice Chapter: Table of Contents

Medical Group(s)
  Enter Federal ID number
    Enter Provider's name
    Enter Legal Practice Name
  ⊘ Summary of Medical Group information Department(s)
  Where do providers see patients?
    Enter additional departments
    Enter office name
    Enter office address
    Enter hospital name
    Enter hospital address
    Enter POS name
    Enter POS address
  ⚠ Summary of Department information Provider(s)
  Enter Provider
    Signature on File
  ⊗ Summary of Provider Information Chapter Review

[ Start Practice Chapter >> ]

FIG. 4C

Page 1

Setting up your Medical Group(s)

A medical group is the entity that receives payments from patients and payors. Your practice may have more than one medical group, depending on how it is structured. However, most small groups have only one.

*For example:*

ABC Medical Group has two physicians, Jane Doe and John Smith. Insurance companies issue payment for both physicians to ABC Medical Group, Inc. As there is one financial entity, there is one medical group.

XYZ Medical Associates has two physicians, Sally Smart and Jack Jones. While both physicians share the same staff and office space, insurance companies issue payment for each physician separately. Checks for Dr. Smart are made to Sally Smart, M.D., P.C.; checks for Dr. Jones are made to Jack Jones, M.D., LLC. As there are two financial entities, there are two medical groups.

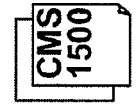 On the CMS-1500 claim form, the medical group information appears in Box 33. Medical group information also appears on patient forms printed from athenaNet, such as patient receipts and encounter forms.

Page 2

Enter your Federal ID Number

A medical group is defined by a Federal Identification Number. This number could be a Tax ID or a provider's Social Security Number. Tell me more Please enter your practice's Federal Identification Number:

[                    ]

Tell me more:
If your practice has been incorporated as a business, you should have a legal business name and a Tax ID. In some states, it's possible that a Tax ID was issued using the founding provider's social security number. In this case, the number is still a business Tax ID and you should choose the button indicating "This number is a business Tax ID."

◎ This number is a provider's SSN.
◎ This number is business' Tax ID.

If you have more than one medical group, you will be asked to enter this medical group after you've finished entering information about your first medical group.

[ << Back ]                                    [ Continue >> ]

FIG. 4E

Enter Provider's Name

You've entered Social Security Number<insert SSN> as your Federal ID number. This means that your Medical Group is a provider. Please enter the provider below.

Page 3

First Name: [          ]

Middle Name: [          ]

Last Name: [          ]

Suffix: [          ]

Degree: [drop down menu ▷]

Medical Group Membership: [Drop down menu ▷]

Specialty: [          ▷]

Taxonomy: [choose]

<u>Tell me more</u>
Taxonomy is used in electronic claims to indicate a provider's type, classification, and area of specialization. A provider's taxonomy often affects a payor's adjudication of a claim.

<u>Tell me more</u>

Do you have another Medical Group?  [YES]  [NO]

[<< Back]

FIG. 4F

Page 4

Enter Legal Practice Name

You've entered Tax ID <insert Tax ID> as your Federal ID number. This means that your Medical Group is a business.

Please enter the legal name of your practice: Tell me more

Tell me more:
If your practice has been incorporated as a business, you should have a legal business name. The business name is likely to include a designation such as LLC, PA, PC, or LLP unless it was incorporated as a sole proprietorship. Make sure you enter the name of the practice as you are known to the IRS.

Practice Name [                    ]

Do you have another Medical Group?

[ YES ]  [ NO ]

[ << Back ]

FIG. 4G

Summary of Medical Group Information

Page 5

| | Medical Group Name | Fed ID Number | ID Type |
|---|---|---|---|
| ⚠ update/delete | John Q. Smith, M.D. | 483-90-8765 | SSN |
| update/delete | Sally Smart, M.D. | 433288876 | Tax ID |
| | add Medical Group | | |

Continue to Next Section >>

FIG. 4H

Page 6

Setting up your Department(s)

Departments allow a practice to schedule patient appointments and bill provider services by location. A department is comprised of a facility name, address, and "place of service code" on claims sent to an insurance company.

A practice can have several departments depending on the various places providers see patients AND multiple departments can exist for the same location, depending on the types of services performed at that location.

*For example:*
Sally Smart is a general surgeon at XYZ Medical Associates. Three days a week, Dr. Smart sees patients in the office. The remainder of her week is devoted to performing inpatient and outpatient surgeries at Central Street Hospital and treating Central Street Hospital emergency room cases. Dr. Smart also performs outpatient surgeries at the Central Street Surgical Center three days a month.

Dr. Smart provides services at three locations: XYZ Medical Associates, Central Street Hospital, and Central Street Surgical Center; however, as her Central Street Hospital services can be inpatient, outpatient, or emergency room, Dr. Smart actually has FIVE departments:

- XYZ Medical Associates
- Central Street Hospital - Inpatient
- Central Street Hospital - Outpatient
- Central Street Hospital - ER
- Central Street Surgical Center

 On the CMS-1500 claim form, department information will appear in Boxes 24B and 32.

<< Back    Continue >>

FIG. 4I

Where do your providers see patients?

Page 7

Please check each box that applies:

☐ Office
☐ Hospital
☐ Other

<< Back          Continue >>

FIG. 4J

Page 9

Enter office name

You indicated that your providers see patients in an office. Please tell us how you refer to your office by name. For example, many practices use the name "Main office" to designate their primary office location or they may name it after the street address (e.g., Pine Street office). The name you assign here will appear in all "Department" drop down menus in athenaNet so make sure you assign names that will enable you to differentiate between office locations Office Name [          ]

HINT: To ensure your drop down menus are reasonable in size, you may want to abbreviate this name, limiting it to 20 characters or less.

Please enter the name of the office as you want it to appear on claims. This should be the "official" name of the office, as it is known to payors. Typically, this is the name of your medical group (e.g., XYZ Medical Associates)

Billing Name [          ]

If you have more than one office, you will be asked to enter this information after you've finished entering information about your first office.

[<< Back]                                                [Continue >>]

FIG. 4K

Enter office address

Page 10

Office Name — Show name as entered from previous page

Address 1

Address 2

Zip Code

City

State

Phone

Fax

Do you have another office?

YES    NO

<< Back

FIG. 4L

Page 11

Enter hospital name

You indicated that your providers see patients in a hospital. Please tell us how you refer to the hospital. The name you assign here will appear in all "Department" drop down menus in athenaNet.

Hospital Name [          ]

HINT: To ensure your drop down menus are reasonable in size, you may want to abbreviate this name, limiting it to 20 characters or less.

Please select the types of departments in which you provide care at this hospital. Most physicians provide care in more than one of the following contexts within one hospital.

☐ Inpatient   ☐ Outpatient   ☐ Emergency Room

Please enter the name of this hospital department as you want it to appear on claims. This should be the "official" name of the hospital, as it is known to payors (e.g., Central Street Hospital)

Billing Name [          ]

If your providers see patients at more than one hospital, you will be asked to enter this information after you've finished entering information about the first hospital.

[ << Back ]                                           [ Continue >> ]

FIG. 4M

Page 12

Enter hospital address

Hospital Name   Show name as entered from previous page

Address 1

Address 2

Zip Code

City         Phone

State        Fax

Do you see patients in another Hospital?

YES    NO

<< Back

FIG. 4N

Enter additional places of service

Page 8

You indicated that your providers see patients in a location OTHER THAN an office or hospital.

Please select additional places of service from the list below:

- ☐ AMBULANCE - AIR OR WATER [42]
- ☐ AMBULANCE - LAND [41]
- ☐ AMBULATORY SURGICAL CENTER [24]
- ☐ ASSISTED LIVING [13]
- ☐ BIRTHING CENTER [25]
- ☐ COMMUNITY MENTAL HEALTH CENTER [53]
- ☐ COMPREHENSIVE INPATIENT REHABILITATION FACILITY [61]
- ☐ COMPREHENSIVE OUTPATIENT REHABILITATION FACILITY [62]
- ☐ CUSTODIAL CARE FACILITY [33]
- ☐ END STAGE RENAL DISEASE TREATMENT FACILITY [65]
- ☐ GROUP HOME [14]
- ☐ HOSPICE [34]
- ☐ INDEPENDENT LABORATORY [81]
- ☐ INTERMEDIATE CARE FACILITY/MENTALLY RETARDED [54]
- ☐ MILITARY TREATMENT FACILITY [26]
- ☐ NURSING FACILITY [32]
- ☐ PATIENT HOME [12]
- ☐ PSYCHIATRIC FACILITY - INPATIENT [51]
- ☐ PSYCHIATRIC FACILITY - OUTPATIENT [52]
- ☐ PSYCHIATRIC FACILITY - RESIDENTIAL TREATMENT CENTER [56]
- ☐ RESIDENTIAL SUBSTANCE ABUSE TREATMENT FACILITY [55]
- ☐ RURAL HEALTH CLINIC [72]
- ☐ SKILLED NURSING FACILITY [31]
- ☐ STATE OR LOCAL PUBLIC HEALTH CLINIC [71]
- ☐ URGENT CARE FACILITY [20]

Continue >>

<< Back

FIG. 40

Page 13

Tell me more:
The place of service code is tied to payor reimbursement schedules. It's important that you use the proper code for each place of service at which medical services are rendered.

Enter "Place of Service" (POS) name

You indicated that your providers see patients in the following type of facility: <ENTER TYPE CHOSEN ON PREVIOUS PAGE>. Oops, I picked the wrong one Please tell us how you refer to this place of service by name. You may use an informal name. It needs to be recognizable by all staff who will be using athenaNet, but does not need to be an "official" facility name. The name you assign here will appear in all "Department" drop down menus in athenaNet.

POS Name [          ]

HINT: To ensure your drop down menus are reasonable in size, you may want to abbreviate this name, limiting it to 20 characters or less.

Please enter the name of this place of service as you want it to appear on claims. This should be the "official" name of the place of service, as it is known to payors. Tell me more

Billing Name [          ]

If you chose more than one place of service on the previous page, you will be asked to enter this information after you've finished entering information about the first place of service.

[<< Back]   [Continue >>]

FIG. 4P

Enter POS address

Page 14

POS Name — Show name as entered from previous page

Address 1

Address 2

Zip Code

City

State

Phone

Fax

Do you have another <insert place of service type>?

[ YES ]   [ NO ]

[ << Back ]

FIG. 4Q

Page 15

Summary of Department(s)

| | Department Name | Place of Service Type | Billing Name | Address | |
|---|---|---|---|---|---|
| update/ delete | Pine Street | Office | Pine Street Medical Associates | 289 Pine Street Springfield, IL 47839 | (765)889-7838 (765)338-9939 |
| update/ delete | Oak Hospital | Inpatient Hospital Outpatient Hospital Emergency Room | Oak Hospital | 10 Main Street Springfield, IL 47839 | (765)883-8838 (765)858-8845 |
| update/ delete | Longwood | Birthing Center | Longwood Birthing Center | 1045 Webster Street Springfield, IL 47339 | (765)889-3993 (765)858-8907 | add another department

⚠ Example of warning: "You indicated that you had the following place of service type: <insert type of POS>, but you have not entered any data about this facility. If you want to delete this place of service type...."

[ Continue to Next Section >> ]

FIG. 4R

Page 16

Add New Department

What type of department would you like to add?

◎ Office

◎ Hospital

◎ Other

FIG. 4S

Page 17

Setting up your Providers

A provider is a practice staff member who submits claims to payors for patient services or requires a schedule for patient appointments. While any provider can have an appointment schedule, only certain providers can be credentialed to bill claims; therefore, your list of practice providers may be longer than your list of credentialed clinicians.

There are two different types of providers: physician providers and mid-level providers. Physician providers have a MD or DO degree and, typically, are credentialed with payors to bill claims under their own name. Mid-level providers are non-physician clinicians, such as nurse practitioners, physician assistants, or technicians. Most mid-level providers are not credentialed and bill for patient services under a physician, although some states and payors do allow mid-levels to bill for their own services.

If SSN medical group, show following:
Remember, you already entered <b><Dr. Last Name></b> during medical group setup. You <b>do not</b> need to enter him as a provider because he has already been entered.

<< Back                    Continue >>

FIG. 4T

Page 18

Enter Provider

First Name

Middle Name

Last Name

Suffix

Degree — drop down menu

Medical Group Membership — Drop down menu

Specialty —

Taxonomy — choose

Tell me more
Taxonomy is used in electronic claims to indicate a provider's type, classification, and area of specialization. A provider's taxonomy often affects a payor's adjudication of a claim.

Tell me more

Do you have another provider to enter?

YES   NO

<< Back

FIG. 4U

Page 19

Signatures on file?

HIPAA regulations require that you have signatures on file for each of your providers who bill for services. Please check the box next to each provider for whom you have signatures on file.

☐ Provider full name, Degree

☐ Provider full name, Degree......

Continue >>

<< Back

FIG. 4V

Summary of Provider Information

Page 20

| | Provider Name | Specialty | Taxonomy | Provider Type | Medical Group |
|---|---|---|---|---|---|
| update/ delete | Mike W. Smith, MD | Internal Medicine | Osteopathic & Allopathic: | MD | Medical Associates |
| update/ delete | Jean A. Jones, MD | Family Practice | Osteopathic & Allopathic: | MD | Medical Associates |
| update/ delete | Stephanie Block, NP | Family Practice | | NP | |
| update/ delete | John P. Ellis, RN | Family Practice | | RN | | add another provider

End of Practice Chapter

You have reached the end of the Practice chapter.

If you would like to review your work before proceeding, use the links below:

Medical Group Summary
Department Summary
Provider Summary

If you believe you are done with this chapter, please click 'I'm done!'.

I'm done!

Page 21

FIG. 4X

Page 22

Review of Practice Chapter

Congratulations! Your work in the Practice chapter is free of errors.

Your Account Manager will review the work you have done and you will be notified when you can move on to the next Chapter.

FIG. 4Y

Page 23

Review of Practice Chapter

The <insert section name> section still contains errors. You cannot mark this chapter as done until these errors have been fixed. Please click each link below to return to the Summary page and fix errors."

<section name> Summary

If you need help, please send a message to your Account Manager.

Page 24

Review of Practice Chapter

Please review the following warnings. If you need to make corrections, click on the appropriate link. If you do not need to make corrections, please click OK.

In the Medical Group(s) section......<insert warning>
 In the Provider(s) section......<insert warning>
 In the Provider(s) section......<insert warning>

[ OK ]

AUTOMATED CONFIGURATION OF MEDICAL PRACTICE MANAGEMENT SYSTEMS

CROSS REFERENCE TO RELATED APPLICATIONS

This application is a continuation of U.S. patent application Ser. No. 12/408,561 filed on Mar. 20, 2009, which is a continuation of U.S. patent application Ser. No. 11/779,926 filed on Jul. 19, 2007, which claims the benefit of and priority to U.S. Provisional Patent Application No. 60/832,073, filed on Jul. 20, 2006, the disclosures of all of which are hereby incorporated by reference in their entireties.

TECHNICAL FIELD

The present invention relates generally to methods and systems, including computer program products, for automated configuration of medical practice management systems.

BACKGROUND

Before the advent of networked systems and computers, medical patient workflow and billing was a manual process. Doctors, nurses, and receptionists used paper-based records to keep track of which tests a patient had undergone, what the patient's insurance would and would not cover, and how claims for healthcare items and/or services would be settled. As computers became more widely utilized, many medical practitioners used computers for electronic record keeping and billing statement generation.

With many medical practices, the number of patients that the practice serves fluctuates from day to day or season to season. As a result, the number and/or complexity of transactions that a medical practice management system processes for a given time period also fluctuates. These transactions, however, are important to the proper functioning of a medical practice management system. Examples of transactions include patient eligibility for a payment with respect to healthcare items and/or services, referral verification and approval, and claims processing transactions. When interacting with third-party payors such as insurance companies, it is often difficult to determine if the payors' processing system can handle a given volume of data that needs to be processed for the medical practice management system to function.

SUMMARY OF THE INVENTION

One approach to automated computerized configuration of medical practice management systems is a method. The method includes receiving first information associated with a medical practice. One or more requests for second information are generated based on the first information and/or one or more insurance rules that apply to one or more payor servers, which are associated with the medical practice based on the first information. Second information, which comprises information for submission of medical claims to the one or more payor servers, is received based on the one or more requests for second information. Configuration information for the medical practice management system is generated based on the first information and/or the second information.

Another approach to automated computerized configuration of medical practice management systems is a computer program product. The computer program product is tangibly embodied in an information carrier. The computer program product includes instructions being operable to cause a data processing apparatus to receive first information associated with a medical practice. One or more requests for second information are generated based on the first information and/or one or more insurance rules that apply to one or more payor servers, which are associated with the medical practice based on the first information. Second information, which comprises information for submission of medical claims to the one or more payor servers, is received based on the one or more requests for second information. Configuration information for the medical practice management system is generated based on the first information and/or the second information.

Another approach to automated computerized configuration of medical practice management systems is a system. The system includes a medical practice module and a server configuration module. The medical practice module is configured to receive first information associated with a medical practice. The medical practice module is further configured to receive second information, which comprises information for submission of medical claims to one or more payor servers, based on one or more requests. The server configuration module is configured to generate the one or more requests for the second information based on the first information and/or one or more insurance rules that apply to the one or more payor servers, which are associated with the medical practice based on the first information. The server configuration module is further configured to generate configuration information for the medical practice management system based on the first information and the second information.

Another approach to automated computerized configuration of medical practice management systems is a system. The system includes a means for receiving first information associated with a medical practice. The system further includes a means for receiving second information, which comprises information for submission of medical claims to one or more payor servers, based on one or more requests. The system further includes a means for generating the one or more requests for the second information based on the first information and/or one or more insurance rules that apply to the one or more payor servers, which are associated with the medical practice based on the first information. The system further includes a means for generating configuration information for the medical practice management system based on the first information and the second information.

In other examples, any of the approaches above can include one or more of the following features. The configuration information comprises information utilized to select third information for submission to a payor server and/or information utilized to format the selected third information for submission to the payor server. The configuration information is merged with stored configuration information for the medical practice. The stored configuration information for the medical practice is replaced with the configuration information.

In some examples, whether to request additional information is determined based on the first information, the second information, and/or the one or more insurance rules that apply to the one or more payor servers. One or more requests for additional information is generated based on the first information, the second information, and/or the one or more insurance rules that apply to the one or more payor servers. Additional information, which comprises information for submission of medical claims to the one or more payor servers, is received based on the one or more requests for additional information. Configuration information for the medical practice management system is generated based on the first information, the second information, and/or the additional information.

In other examples, the first information and the second information are being received from a user. A user interface is dynamically updated based on the first information and/or the second information.

In some examples, the first information includes medical group information, tax information, provider information, legal information, department information, patient information, medical office information, hospital information, place of service information, signature information, user information, and/or user permission information. The second information includes payor information and/or information associated with an insurance rule.

In other examples, the first information is different from the second information. The first information, the second information, and/or the configuration information is stored in a medical practice information database. One or more user interfaces for one or more users of the medical practice are generated based on the configuration information. The one or more users are healthcare professionals associated with the medical practice.

In some examples, one or more rules for the medical practice management system are generated based on the configuration information. The first information and/or second information are checked to determine if one or more errors are associated with the first information and/or second information. The one or more errors includes incorrect information and/or missing information.

In other examples, one or more requests are generated for correct information. Correct information is received based on the one or more requests for correct information. One or more rules associated with one or more payor servers are utilized to check the first information and/or the second information.

In some examples, the configuration information includes medical claim processing information associated with the medical practice, medical claim processing information associated with one or more payor servers, and/or medical claim information utilized to generate medical claims for submission to one or more payor server.

In other examples, a medical practice information database is configured to store the first information, the second information, and/or the configuration information. The server configuration module is further configured to check the first information and/or second information to determine if one or more errors are associated with the first information and/or second information.

In some examples, the server configuration module is configured to generate one or more requests for correct information and receive correct information based on the one or more requests for correct information.

Any of the approaches and examples above can provide one or more of the following advantages. An advantage is that a medical practice can quickly and efficiently configure the medical practice management system for the individualized needs of the medical practice. Another advantage is that the cost of configuring and setting up medical practice management systems for medical practices is significantly reduced through the use of the automated configuration. An additional advantage is that the medical practice management system can be quickly and efficiently changed based on changes to the medical practice. Another advantage is that a user that is not experienced with the system can quickly and accurately customize the system for the user's medical practice which decreases the cost of switching to the system.

BRIEF DESCRIPTION OF FIGURES

The foregoing and other objects, features, and advantages of the present invention, as well as the invention itself, will be more fully understood from the following description of various embodiments, when read together with the accompanying drawings.

FIGS. 4A-4Z are each an exemplary screenshot of a client interface in a medical practice module.

DETAILED DESCRIPTION

Automating medical practice workflow and billing presents difficulties in many aspects including installation of a system, processing the eligibility or other status information of patients, interacting with the workflow, with other health care providers, and within the constraints of payor requirements, as well as measuring the success of a practice once the workflow has been established.

In accordance with Applicant's technology, a user (e.g., medical office manager, medical office insurance administrator, doctor) utilizes a medical practice configuration interface (e.g., web page) to input information about the user's medical practice (e.g., address, insurance plans, doctors, hospitals that the doctors utilize). Based on this information and/or rules associated with the insurance plans accepted at the user's medical practice, additional information is requested from the user about the user's medical practice (e.g., information needed for an insurance plan, information needed for a hospital). The user inputs the requested additional information utilizing the medical practice configuration interface. Configuration information for the user's medical practice is generated based on the information and/or the additional information inputted by the user. A user interface (e.g., web pages interfacing with the medical practice management server) and/or rules for the medical practice can be generated based on the configuration information.

For example, a medical office manager uses the web interface of the medical practice management system to input the medical practice's address, doctor information, hospital association information (in this example, the doctors have access to Big City Hospital), and insurance company information (in this example, medical practice accepts insurance plan Omega). The medical practice management system checks the inputted information using one or more rules associated with the hospital and the insurance companies. Big City Hospital requires the Drug Enforcement Administration (DEA) number for each of the doctors associated with the hospital. Insurance plan Omega requires information about whether the medical practice accepts nonpaying patients (e.g., charity patients). The web interface requests the DEA number for each doctor and whether the medical practice accepts nonpaying patients. The medical office manager inputs the DEA number for each doctor and indicates that the medical practice will accept selected nonpaying patients (e.g., referred by a charitable organization). The medical practice management system generates configuration information based on the information inputted by the user about the medical practice. The configuration information is utilized by the medical practice management system to generate user interfaces for the system and/or rules for the medical practice (e.g., send the doctor's DEA number with every prescription order to the Big City Hospital).

Figure 1:
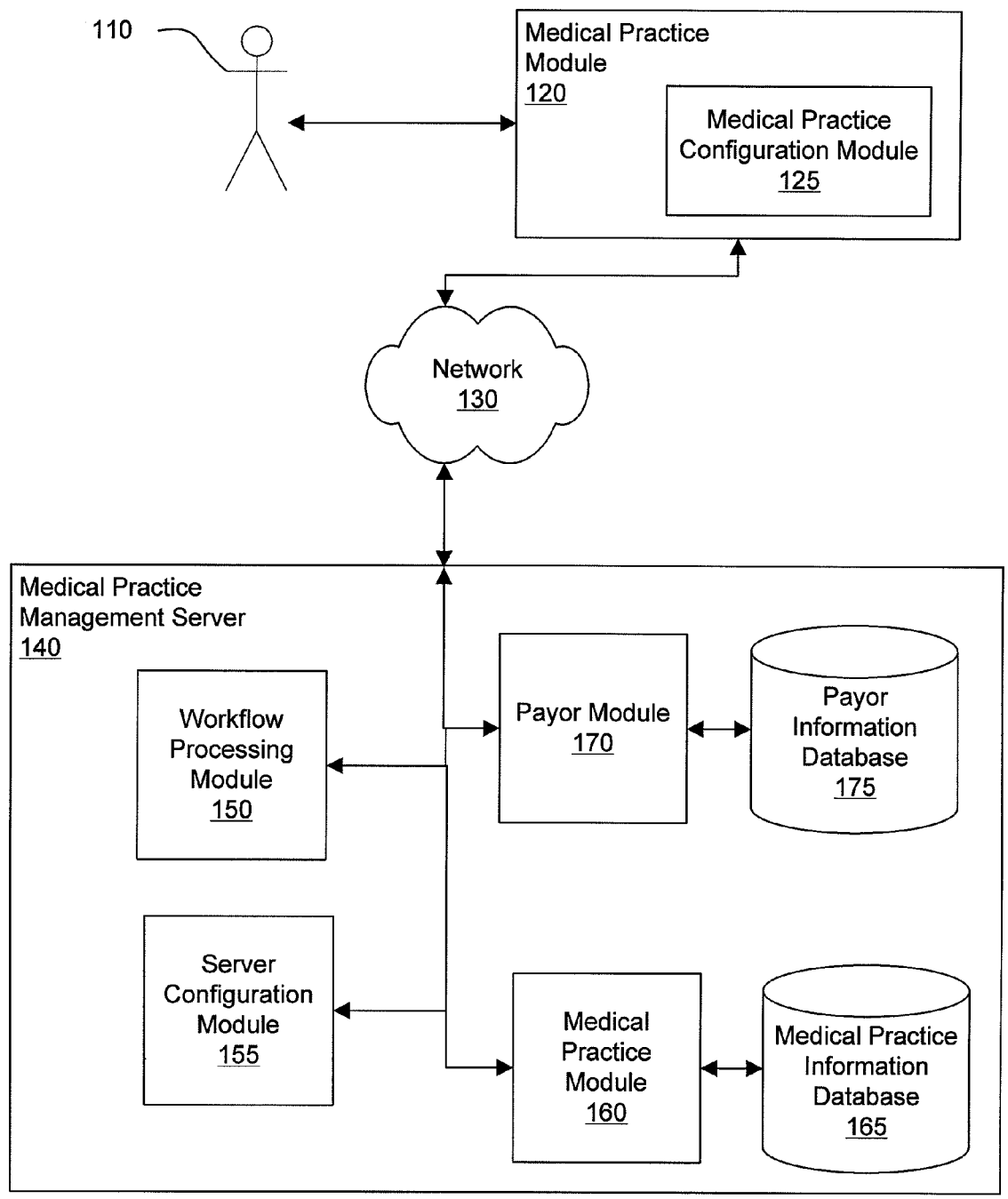
FIG. 1 is a functional block diagram of an exemplary system illustrating a medical practice management system.

FIG. 1 is a functional block diagram of an exemplary system 100 illustrating a medical practice management system. The exemplary medical practice management system 100 includes a user 110, a medical practice module 120, a network 130, and a medical practice management server 140. The medical practice module 120 includes a medical practice configuration module 125. The medical practice management server 140 includes a workflow processing module 150, a server configuration module 155, a medical practice module 160, a medical practice information database 165, a payor module 170, and a payor information database 175.

The user 110 utilizes the medical practice module 120 to communicate through the network 130 to the medical practice management server 140. To setup the system 100 for use by the user's medical practice and/or to modify the setup of the system 100 based on changes to the user's medical practice, the user 110 communicates information about the medical practice to the server configuration module 155. The server configuration module 155 generates requests for additional information based on the information from the user 110. The user 110 communicates additional information in response to the requests from the server configuration module 155.

The server configuration module 155 generates configuration information for the medical practice based on part or all of the information received from the user 110 about the medical practice. The server configuration module 155 generates a user interface and zero or more rules for the medical practice based on the configuration information.

In some examples, the configuration information is communicated to the medical practice module 160 and/or stored in the medical practice information database 165. The medical practice module 160 can utilize, for example, the configuration information to configure the medical practice management system 100 for the users at the medical practice. The configuration of the medical practice management system 100 for each medical practice includes, for example, the use of the names, addresses, doctor information, and/or other information associated with the medical practice of the user by the system 100 for interactions with the user.

In other examples, the configuration information includes information for submitting medical claims to payors from the medical practice. For example, insurance company Beta requires that all medical practices in Massachusetts submit the physical address of the office in which the patient encounter occurred and the billing address for the medical practice. When the medical office manager 110 for medical practice Alpha configured the medical practice management system 100 for the medical practice, the server configuration module 155 requested the physical address of each medical practice office in Massachusetts from the medical office manager 110. This information, the physical addresses of each medical practice office in Massachusetts, is part of the configuration information for medical practice Alpha and can be stored in the medical practice information database 165.

Although FIG. 1 illustrates only one user 110 from one medical practice utilizing the medical practice management system 100, a plurality of users (e.g., 110) can utilize the medical practice management system 100 to setup the system 100 for use by that user's medical practice. For example, Sue Allen, office manager of Feet are Us Docs, accesses the server configuration module 155 through a medical practice module A (not shown) to setup the medical practice management system 100 for Feet are Us Docs medical practice. Paul Stevens, office manager of Feet Specialists of Detroit, accesses the server configuration module 155 through a medical practice module B (not shown) to setup the medical practice management system 100 for the Feet Specialist of Detroit medical practice. The users (e.g., doctors, receptionists, administrators) of each medical practice can access the medical practice management system 100 customized for their particular medical practice, Feet are Us Docs and Feet Specialist of Detroit.

In some examples, the user interface includes one or more web pages that are utilized to display and/or receive information to/from the user 110. The user interface can be, for example, dynamically created based on the configuration information and/or the user permissions. The user interface can be, for example, created based on the configuration information and/or user group permissions (e.g., office administrator group, insurance administrator group, receptionist group, doctor group). The user interface and/or information associated with the user interface can be, for example, stored in the medical practice information database 165. In some examples, the user interface includes an application (e.g., JAVA applet) executing on the user's computer.

In other examples, the zero or more rules for the medical practice include rules for the processing of patient encounters, insurance claims, and/or any other type of patient interaction with the medical practice (e.g., billing). For example, the practice manager 110 at Dentists for Everyone communicates information to the server configuration module 155 that a copy of the primary insurance holder's driver's license is required for all insurance claims from Dentists for Everyone. When George Allen, the primary insurance holder, brings his son, J. J. Allen, to Dentists for Everyone for a dental checkup, the receptionist will ask George Allen for a copy of his driver's license. If the receptionist does not input (e.g., upload the image, verify that the copy was made and is in the patient file) the copy of George Allen's driver's license into the medical practice management system 100, then the rule requiring the copy of the license will not allow the checkout of George Allen and his son to occur.

As another example, the practice manager 110 at Radiology Associates of X-Ray communicates information to the server configuration module 155 that only users in the insurance administrators group can submit medical claims to the payor servers. Based on this information, the server configuration module 155 creates a rule for Radiology Associates of X-Ray that does not allow the submission of medical claims (e.g., insurance claim for payment) to payor servers (e.g., insurance company servers) unless the user is a member of the insurance administrator group.

In some examples, the network 130 is a wide area network (WAN) connecting a plurality of medical practice offices to the medical practice management server 140 and/or a medical practice management network. The network 130 can be, for example, a public communication network (e.g., Internet) and/or a private communication network (e.g., Intranet).

In other examples, the medical practice management server 140 is a web server hosting a web application that the user 110 utilizes to submit and/or access information associated with the user's medical practice. The medical practice management server 140 can be, for example, an information interface that communicates information from a medical practice client application on a computing device 120 that the user 110 utilizes to submit and/or access information associated with the user's medical practice.

The patient and/or clinic workflow can be, for example, processed by the workflow processing module 150. Although FIG. 1 illustrates workflow functionality via the workflow processing module 150, other examples provide workflow functionality via a message passing interface (not shown). The message passing interface can be utilized, for example, to communicate between the user 110 and the medical practice management server 140.

In some examples, the medical practice is the office of the medical care provider (e.g., a doctor's office), a hospital, and/or any other facility for medical encounters. Although also referred to as an insurance company, the payor organization can include, for example, health maintenance organizations (HMOs). Payor organizations include, for example, Century Health and Benefits, HMO Blue, Harvard Pilgrim Health Care, MassHealth, Medicare, Neighborhood Health Plan, Tufts Associated Health Plan, and/or United Healthcare.

Before a medical practice can take advantage of the medical practice management system 100, the system 100 is generally configured to work with the medical practice. In some examples, the server configuration module 155 includes an automated practice management configuration tool. For example, a user 110 (e.g., a practice management consultant, employee of the medical practice) utilizing a user interface, typically displayed on a Liquid Crystal Display (LCD) or Cathode Ray Tube (CRT), with a series of display screens that assist in configuring a medical practice management system 100. The user 110 is prompted for input (e.g., mouse clicks, keyboard presses) and the tool determines what the next prompt for information is based on the input provided by the user 110.

In some examples, information that is provided by the user 110 to the tool when setting up the medical practice includes, but is not limited to, where the medical practice is located, offices or providers associated with the medical practice that are or are not located at the location previously specified, departments, facilities, registration with insurance companies, registrations with government programs such as Medicaid, Medicare, and/or Clinical Laboratory Improvement Amendments (CLIA), a federal identification number associated with the practice, prior and existing patient appointments, prior medical services provided, claim processing history, as well as contact information and/or other information associated with the medical practice.

The screens present questions that are generally easy to answer for anyone familiar with the medical practice. Beneficially, there is little to no need for expensive business analysts or system consultants to configure the system. Based on the answers provided by the user, the tool then configures the medical practice management system. In some examples, configuring the medical practice management system involves creating, updating, dropping, and/or modifying databases, tables, views, and/or stored procedures in a database, and rows and/or columns in a database table and the like.

The information received by the server configuration module 155 and/or the medical practice module 120 includes medical group information, tax information (e.g., tax id), provider information, legal information, department information, patient information, medical office information, hospital information, place of service information, signature information, user information, user permission information, payor information, information associated with an insurance rule, and/or any other information associated with a medical practice.

Figure 2:
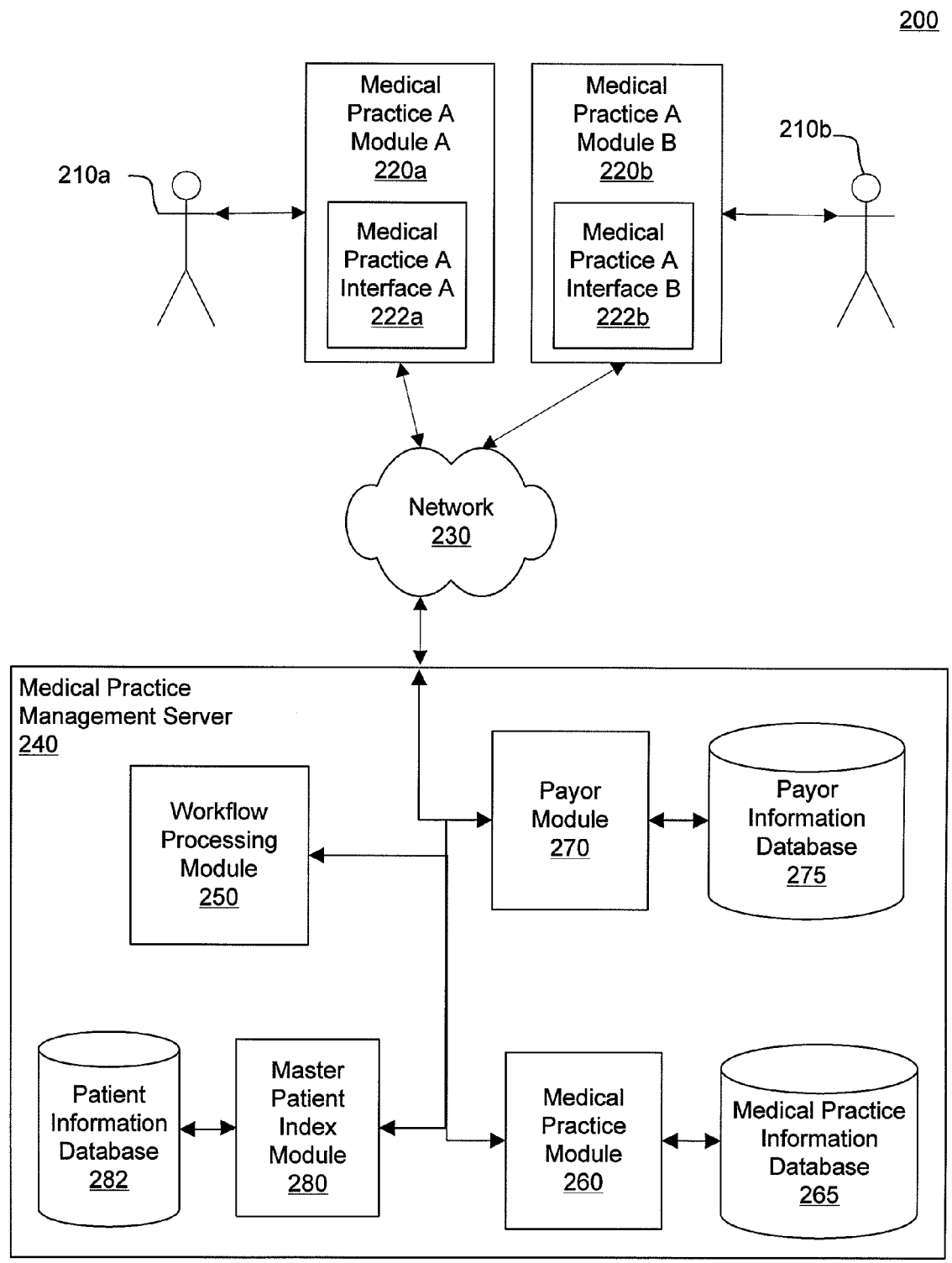
FIG. 2 is a functional block diagram of an exemplary system illustrating a medical practice management system with multiple users.

FIG. 2 is a functional block diagram of an exemplary system 200 illustrating a medical practice management system with multiple users 210a and 210b. The exemplary medical practice management system 200 includes the users 210a and 210b (e.g., healthcare professionals associated with the medical practice) who utilize medical practice A modules A 220a and B 220b, respectively. The medical practice A modules 220a and 220b include medical practice A interfaces A 222a and B 222b, respectively. The medical practice A modules A 220a and B 220b communicate with the medical practice management server 240 through a network 230.

The medical practice management server 240 includes a workflow processing module 250, a medical practice module 260, a medical practice information database 265, a payor module 270, a payor information database 275, a master patient index module 280, and a patient information database 282. The workflow processing module 250 processes the workflows of the patients and/or the office. The medical practice module 260 processes the configuration information stored in the medical practice information database 265, the user interface of each medical practice, and/or rules associated with each medical practice. The payor module 280 processes insurance claims for submission to the payor servers based on one or more insurance rules stored in the payor information database 275. The master patient index module 280 processes requests for patient information and retrieves patient information from the patient information database 282.

For example, the doctor 210a and the receptionist 210b at the Great Feet Doctors of West Iowa medical practice access the medical practice manager system 200 utilizing medical practice modules A 220a and B 220b. The medical practice modules 220a and 220b are each of the users 210a and 210 respective desktop personal computers that have a web browser operating on them (in this example, medical practice interface A 222a and B 222b which are web sites that include web pages configured for each user). The doctor 210a can utilize her computer 220a to access the web site 222a that is configured for the doctor 210a (e.g., patient tests, patient test results). The receptionist 210b can utilize her computer 220b to access the web site 222b that is configured for the receptionist 210b (e.g., patient schedule, referral schedule).

Parts or all of the web site 222a or 222b can be, for example, dynamically created based on the configuration information and/or rules for the medical practice. For example, the basic design for the doctor web site 222a is pre-configured to include patient test and patient test result sections based on information inputted during the configuration of the medical practice. Based on the information inputted during the configuration of the medical practice, the display of referrals for doctors is dependent on the doctor. When the doctor 210a accesses the web site 222a, the rule for the doctor 210a is to display the referral information for the patient, so the web page that the doctor 210a is viewing is dynamically updated to include the referral information.

Figure 3:
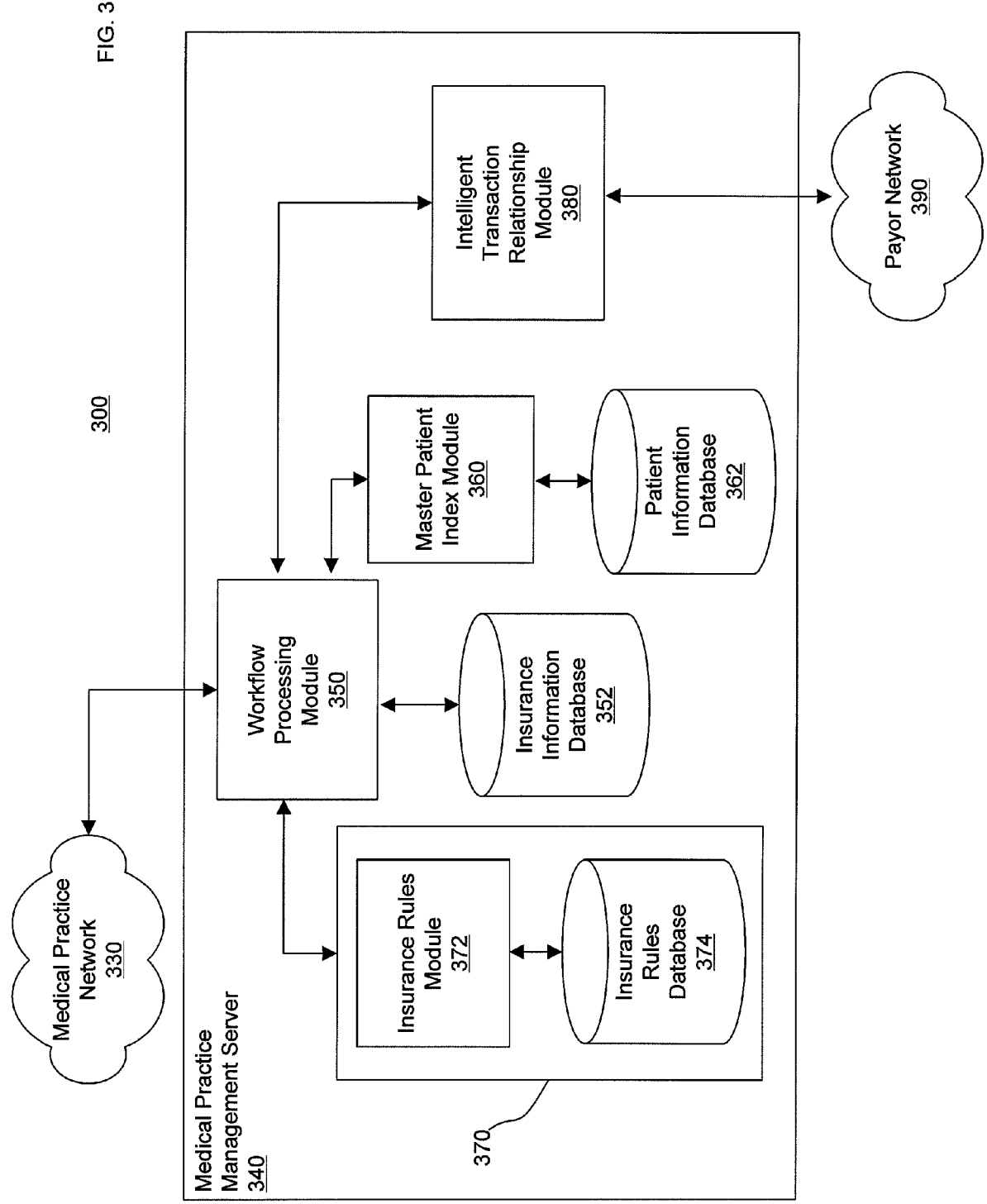
FIG. 3 is a functional block diagram of an exemplary system illustrating a medical practice management server communicating with a medical practice network and a payor network.

FIG. 3 is a functional block diagram of an exemplary system 300 illustrating a medical practice management server 340 communicating with a medical practice network 330 and a payor network 390. The medical practice management server 340 includes a workflow processing module 350, a rules module 370, and an intelligent transactions relationship (ITR) module 380. The rules module 370 includes an insurance rules module 372 and an insurance rules database 374.

The medical practice management server 340 includes a patient information database 362 and an insurance information database 352. The workflow processing module 350 stores part or all of the information associated with a patient in the patient information database 362. The patient information database 362 stores information associated with patients of the medical practice. The information can include, for example, the patient's address, phone number, zip code, height, weight, allergies, previous doctor(s), and/or other information associated with the patient.

In some examples, the workflow processing module 350, the rules module 370, and/or the ITR module 380 are software modules located within the medical practice management server 340. In other examples, the workflow processing module 350, the rules module 370, and/or the ITR module 380 are externally located from the medical practice management server 340 and communicate with the medical practice management server 340. In other examples, the rules module 370 includes a patient rules module (not shown) that processes rules associated with patients, and/or other types of rule modules that process rules associated with healthcare.

In some examples, the workflow processing module 350 is a software application that controls and manages the features and functions of the medical practice management server 340. The workflow processing module 350 and the medical practice module (not shown) communicate over the medical practice network 330. The medical practice module can transmit a medical care provider request containing information to the medical practice management server 340 using, for example, a common gateway interface (CGI) request. For example, when registering a new patient, a medical care provider operating the medical practice module enters the relevant patient information on a patient registration template that the workflow processing module 350 delivered to the medical practice client user interface (not shown).

In other examples, the workflow processing engine 350 validates the structure and composition of information entered by a medical care provider at the medical practice client to ensure that the information is correct (e.g., structure and/or composition). Examples of information entered by a medical care provider at the medical practice client include the patient's address, phone number, medical history, insurance information, diagnosis and procedure codes, and/or other information associated with a healthcare patient.

In some examples, the workflow processing engine 350 communicates with the rules module 370. The rules module 370 enables real-time application of "rules" stored in the rules database (not shown). A rule can be, for example, coded logic that evaluates data and then performs an action.

The rules module 370 can access and update, for example, information stored in the insurance rules database 374 using the insurance rules module 372. Although FIG. 3 illustrates the rules module 370 external to the workflow processing module 350, the rules module 370 can be, for example, a software layer internal to the workflow processing module 350. In some examples, the rules module 370 is implemented as an application program interface, a Component Object Model (COM) object, an Enterprise Java Bean, and/or any other type of database interface module.

The insurance rules database 374 and/or the interface to the insurance rules database 374 can be written, for example, in a structured query language. In some examples, the insurance rules module 372 uses a Lightweight Directory Access Protocol (LDAP) to access information in the insurance rules database 374. Additionally or alternatively, the insurance rules database 374 can be external to the medical practice management server 340 (e.g., distributed across three geographically dispersed data centers) or can be internally situated in the medical practice management server 340.

The insurance rules database 374 includes insurance company rules that define the appropriate format and content of clinical and claim information that the payor server (not shown) processes. In some examples, the rules are subdivided into various classes. For examples, the rules are divided into rules that have universal applicability to all claims for a specified payor, rules that apply only to one or more specific insurance packages from among the variety of insurance packages that the payor offers to medical care providers, and/or rules that apply only to specific medical care providers who provide care under one or more specific insurance packages.

To ensure that the insurance rules database 374 contains current rules, the insurance rules database 374 can be, for example, frequently updated. In some examples, individual payors transmit rule updates/creations to the medical practice management server 340 via their payor server. Rule specialists can, for example, review the rules transmitted by the payor server and subsequently update the insurance rules database 374. In some examples, the rules specialist performs any and all updates to the insurance rules database 374. In other examples, the updating of the insurance rules database 374 can be automated upon receipt of a rule transmission from the payor server or the medical practice client.

In some examples, a medical care provider can submit information to the medical practice management server 340 for subsequent update of the insurance rules database 374 based on the medical care provider's experience with one or more payors. In other examples, the insurance rules database 374 is updated with the server's historical analysis of previously submitted claims, especially those that were denied, to identify the reasons for denial. The historical analysis of previously submitted claims can facilitate the development of new insurance rules for the insurance rules database 374.

In some examples, the medical practice management server 340 indexes the patient information stored in the patient information database 362 by the patient name. In other examples, the medical practice management server 340 indexes the patient information stored in the patient information database 362 with a patient identifier. The patient identifier can be, for example, a random number, a predetermined integer (such as a patient counter), the patient's zip code, the patient's phone number, and/or any other type of identifier associated with a patient. The workflow processing module 350 can access the patient information database 362 using, for example, a master patient index module 360.

In other examples, the workflow processing module 350 stores information associated with an insurance company in the insurance information database 352. The information associated with an insurance company includes the insurance company's address, the amount of insurance coverage for a particular patient, and/or other information associated with an insurance company. In some examples, the workflow processing module 350 can access the insurance information database 352 using an insurance information database module (not shown).

In some examples, as the workflow processing module 350 receives information from the medical practice client, the workflow processing module 350 determines on a real time basis whether all of the required information has been provided and/or whether the information is in the correct format. In the event that there is a deficiency and/or error in the information, the workflow processing module 350 alerts the medical care provider (e.g., receptionist), or user, for additional information and/or to correct the information. In other examples, the workflow processing module 350 corrects the defect and/or error.

For example, if the insurance rules module 372 contains a rule about member identification formatting for a particular payor, the insurance rules module 372 determines the rule in the insurance rules database 374 and communicates the information to the workflow processing module 350. The workflow processing module 350 communicates this information to the medical practice client when a medical care provider (e.g., receptionist) is registering a patient. If the medical care provider (e.g., receptionist) errs, the medical practice management server 340 alerts the medical care provider (e.g., with a warning message) to correct the error. This enables medical care providers to generate claims with no errors (i.e., referred to as clean claims) for the mutual benefit of the medical care provider and the payor. Additionally, the medical care providers can obtain the information associated with an alert while the patient is physically present (e.g., while the patient is still at the hospital, during their encounter, before checking out).

The workflow processing module 350 can be, for example, in communication with the ITR module 380. The ITR module 380 executes transactions sent to and/or received from the payor server via the payor network 390. Thus, the majority of provider/payor transactions can be accomplished electronically, with little or no human intervention. Examples of these transactions include, without limitation, claim submittals, claim receipt acknowledgements, claim status checks, patient eligibility determinations, authorization and referral requests and grants, and/or remittance advice. For example, a predetermined number of days before a scheduled patient visit, the ITR module 380 automatically checks patient eligibility with the applicable payor identified during the patient registration process. After a patient visit and the completion of the claim template, the claim is submitted to the payor server via the ITR module 380.

In some examples, upon receipt of an insurance claim, the payor transmits a confirmation back to the medical practice management server 340. Later, on a schedule determined by the medical care provider (e.g., weekly, monthly), the ITR module 380 checks the claim status and notifies the medical practice client accordingly. After the ITR module 380 analyzes the claim and generates remittance advice, the ITR module 380 parses the electronic payment and allocates the payment among the individual charge line items for the services provided. Once the medical care provider approves the allocations, the payments are posted to the provider's accounts.

In other examples, insurance rules database 374, insurance information database 352, and/or patient information database 362 are encrypted which advantageously complies with applicable laws and/or regulations. The information stored and/or associated with the medical practice management server 340 can be, for example, encrypted. The encryption of databases and/or information can be, for example, advanced encryption standard (AES), data encryption standard (DES), and/or any other type of encryption method and/or module. The encryption can be, for example, hardware based encryption and/or software based encryption.

In some examples, financial information is removed from the insurance rules database 374, insurance information database 352, patient information database 362, and/or any other information stored and/or associated with the medical practice management server 340. Part or all of the financial information can be, for example, removed and/or hidden (e.g., remove all but the last four digits of the social security numbers). The financial information can be, for example, removed from the primary database where the information is being stored (e.g., patient information database 362) and stored in a separate database. For example, the social security numbers are removed from all patient information stored in the patient information database 362 and placed in the secure patient information database (not shown). The information in the patient information database 362 and the secure patient information database can be associated with each, for example, by utilizing an assigned patient ID. The information in the secure patient information database can be secured, for example, utilizing a password, personal identification number, biometrics, and/or any other security mechanism. The financial information can include, for example, social security numbers, credit card numbers, bank account numbers, and/or any other information associated with finances.

Although FIG. 3 illustrates the modules insurance rules module 372, workflow processing module 350, master patient index module 360, and intelligent transaction relationship module 380 as separate modules, the modules 372, 350, 360, and 380 can be combined, for example, into one module or any number of modules. Similarly, the databases, insurance rules database 374, insurance information database 352, and patient information database 362 can be combined, for example, into one database and/or can be external or internal to the medical practice management server 340.

Figure 4Z:
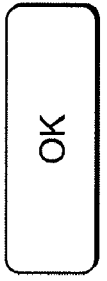
Figure 4Z:
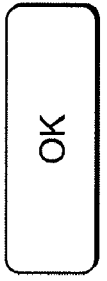
Figure 4Z:
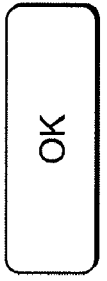

FIGS. 4A-4Z depict one implementation of the automated configuration tool. FIG. 4A depicts a user interface to the tool that a user utilizes to configure the medical practice management system for the medical practice. Areas that are configurable via the tool include, but are not limited to, practice, payors, patients, operations, financials, training, and/or any other type of information associated with a medical practice. Within each area, there are typically sections that have corresponding "tabs" labeled with the section name. For example, as depicted, the area selected is "practice" and the section selected is "departments." Typically, if a user clicks on the section name link, they will go to a configuration page, e.g., a "Setting up . . . " page, for that section. Beneficially, though medical practice is discussed and illustrated, similar features are provided to configure payors, patients, operations, financials, training, and/or any other configuration for a medical practice.

FIG. 4B depicts a table of contents for a practice chapter. The overview illustrates the status of particular sections, the sections indicated by HTML hyperlinks. The hyperlinks allow a user to go directly to particular sections to configure information for that section rather than go through the steps of configuring the system for all aspects of the medical practice each time the tool is used. As depicted in FIG. 4B, the tool has been used to configure multiple aspects of the medical practice (e.g., Medical Groups, Departments, and Providers). A status can be provided, for example, after a particular aspect (in this example, check mark, yield, and issue). When a user completes (or partially completes) any page in a section, the table of contents' summary sections and chapter review page is updated with a green (in this example, check mark), yellow (in this example, yield) or red (in this example, issue) audit symbol to show that a section has been worked on. If one or more errors or warnings exist in a section, a red error symbol is displayed next to the section summary row.

For example, in FIG. 4B, a check mark appears before "Summary of Medical Group Information." The check mark indicates that the Medical Group section has been completed successfully with no validation errors. As depicted, a yield sign with an exclamation point appears next to "Summary of Department Information." The yield sign with an exclamation point typically indicates that the Department section was completed but has inconsistencies and/or errors. The errors can be, for example, incomplete information, incorrect information, and/or any other error. The tool determines if a section has incomplete and/or incorrect information by using business logic associated with configuring the practice to determine that the configuration cannot be completed with the existing provided information. A red circle with an "X" inside the circle appears next to the "Summary of Provider Information" hyperlink indicates that information necessary to configure the system is missing or has not been provided. A clickable button is provided to advance to the next screen.

In some examples, business logic is executed that checks the validity of information when each page is navigated away from (e.g., when a "next" button is pressed, the user wishes to exit the system). In other examples, business logic is executed which checks the validity of the information provided to the tool when all aspects of the section have been completed (e.g., on a section summary page).

In some examples, the first time a user attempts to configure the system for the medical practice, the button displays the text "Start Practice Chapter." Upon a second or subsequent visit, the button displays the text "Resume Practice Chapter." In some implementations, clicking the "Resume Practice Chapter" button navigates the user to the last configuration display the user visited. In some versions, the user is returned to the first configuration display that has errors and/or warnings.

FIG. 4C depicts an introductory screen to the configuration tool that explains a medical group. The screen displayed to the user provides an example explaining the difference between one medical group and two medical groups (e.g., depending on how insurance companies issue payment to the doctors associated with the medical practice). Additionally, information associated with a claim form (in this example, CMS-1500) is explained. Beneficially, relating the information being explained to an existing medical form advantageously increases the user's comfort if the user is familiar with a paper-based claim reconciliation workflow. A user clicks a mouse pointer on the "continue" button, which instructs the tool that the user is ready to view the next screen. The tool processes the click on the continue button and dynamically generates the next screen for the user, in this implementation, a page for entering a Federal ID number.

FIG. 4D depicts a page for entering a Federal ID Number. On the page is a "Tell me more" hyperlink. In any page or display, a user can be presented, for example, with a "Tell me more" link that provides additional useful information to the user. In the example depicted, the "Tell me more" link opens a new window with appropriate text. A Federal ID is typically an alphanumeric sequence and generally limited to twenty (20) characters. If the user does not provide a Federal ID number and clicks the Back button, the user is returned to setting up a medical group page. If the user clicks the Continue button, the user is navigated to the "Enter Practice Name" page.

In some examples, if the user types anything in the Federal ID number field, the user is also required to choose a radio button. If user types in Federal ID number field and clicks "Continue" or "Back" without choosing a radio button, typically a prompt appears informing the user to "Please indicate whether this number is a Social Security Number or a Tax ID." If user chooses SSN, the user is navigated to an "Enter Provider Name" page. If user chooses Tax ID, the user is navigated to an "Enter Legal Practice Name" page.

In other examples, when a user navigates away from a page, validation is performed on the information provided by the user to the tool. Examples of validation rules that may apply to Federal ID number include, but are not limited to: the Federal ID field must be populated and a radio button must be chosen identifying the entry as a Tax ID or a SSN, a Social Security number must be 9 digits and numeric, only characters allowed are two dashes, one after 3 digits, one after 5 digits, and/or a Tax ID must be numeric and contain no characters.

FIG. 4E depicts a page to enter a provider name. In some implementations, some pages provide the ability to add multiple items (e.g., multiple medical providers). To add multiple entries, the user is typically provided with a prompt (e.g., "do you have another X," where X is the item being entered). On these pages, there are typically Yes/No buttons provided so the user can either add another element or not.

On the provider name page, typically the social security number provided to the previous screen is displayed on the provider name page. Exemplary information that the user provides with respect to a provider is first, middle, and last name, any suffixes that apply (e.g., Jr.), degrees the provider holds, the provider's medical group membership and/or their specialty. Additionally, there is a taxonomy input that can be used to provide further detail with regard to the provider's specialty. In some examples, the drop-down menu for degree includes only "M.D." or "D.O." In other examples, medical group name is created using data entered on the provider's name page in the following format: First name, Middle, Last Name, Suffix, Degree. The billed name can be created, for example, using format: First initial, Middle Initial, Last Name (no spaces), Degree (no punctuation).

In some examples, the back button takes the user to the "Enter Federal ID" page where the user is presented with the number they entered and the radio button they previously chose. The user can edit the Federal ID number text field and choose a different radio button. If the user does this, the tool behaves the same as it did after the first entry of information (e.g., navigate the user to the "Enter Provider's Name" page). If the user already provided information on "Enter Provider Name" page, the page typically does not save that data if user clicked the "back" button to navigate away from the "Enter provider's name" page. When the user returns to the "Enter provider's name" page by clicking continue on Federal ID page or by clicking the link on the Table of Contents page, the "Enter provider's name" page is presented and a message stating "you've entered SSN <insert SSN number>..." so the user knows which medical group they were in the process of adding.

If user clicks the Yes button, the user is navigated to the "Enter Federal ID" page which typically appears empty. If user clicks No, the user is navigated to the "Summary of Medical Group Information" page. As with the Federal ID number page, validation is performed against the data entered onto the page. Examples of validation for the provider name page include, but are not limited to, the First name and Last name fields must be populated with letters (periods, single quotes and dashes allowed), and the Degree must have a value (e.g., a selection in the drop down list was chosen).

FIG. 4F depicts a page to enter the Legal Practice Name. The Federal ID number and/or Tax ID can be, for example, displayed from the "Enter Federal ID Number" page. A text field for entering the medical practice name can be, for example, displayed. The back button navigates the user back to the "Enter Federal ID" page which would show the Federal ID number entered and radio button chosen. The Yes button navigates the user back to "Enter Federal ID" page with a blank number field and no radio button chosen. The No button navigates the user to the medical group summary page. Validation for the legal practice name page includes, but is not limited to: practice name must be populated with letters (periods, commas, single quotes, and dashes allowed).

FIG. 4G depicts a summary page for the medical group information section. A summary page for a medical group information section displays one medical group per row. In some examples, the summary page provides update, delete, and/or add functionality for rows displayed on the summary page. Clicking update returns the user to the page where the information was first entered. When using "update," however, for pages that include a "do you have another x?" option, the user is presented with a continue button instead rather than the opportunity to add more elements. Once update has been done, pressing the continue button navigates the user to the summary page.

In some examples, if the user chooses the delete link, a pop up box appears asking, "Are you sure you want to delete this <insert medical group, department or provider, depending on section>?" with OK and Cancel, "OK" being the default option if user hits "Enter." If user clicks OK, the row is deleted from the page. If any data was written to a database during configuration, the information associated with the row inside the database is also deleted. If user clicks cancel, the alert box disappears and user remains on section summary page with no changes.

In other examples, if user wants to add a medical group, department, and/or provider from respective section summary pages, he can click on the link "add <medical group, department, or provider>." The link takes user to first point of the respective medical group, department, or provider entry pages. Summary pages do not typically contain a Back button, though in some versions the summary page does. The user is generally able to use the update link to view previously entered information.

In some examples, on a summary page for a given section, when a user clicks the "Continue to next section" button, validation is performed on the data provided in the current section, e.g., the medical group section, both on the individual data fields (like was performed on the individual pages), and on the summary page data as a whole. Examples of summary page validation include, but are not limited to: the same medical group name cannot exist in more than one row, the same provider name cannot exist in more than one row; the same Federal ID number (SSN or TIN) cannot exist in more than one row, and the practice must have at least one medical group. Depending on the success or failure of the validation logic, statuses are displayed on the summary page.

For example, if all validation rules are passed successfully (i.e., all the data entered is valid data) no alerts are displayed on the summary page. If, however, there was a validation failure for one of the rows, warning symbols are displayed next to the row in which data is missing or invalid. In some examples, text is displayed on the screen when the user moves a mouse cursor over the error symbol. The text can read: "<insert error>. Click the update link to correct problems." If the audit failed because of errors between rows (e.g., two medical groups have the same name) typically an error message is displayed below the summary data (with error symbol to left of message). An example error message includes "You cannot have more than one <insert medical group, provider, or Federal ID number> with the same name. Please correct this error," or alternatively, "Your practice must have at least one medical group. Please enter a medical group."

In some examples, a user is able to continue to the next section without fixing the errors, but the errors will appear again when the chapter validation is performed. In those examples, the user will not be able to complete the chapter without fixing the errors.

In addition to configuring medical group information, department information is configurable. FIG. 4H displays an introduction to the department section, explaining that departments are typically associated with a location. Clicking the continue button navigates the user to the "Where do your providers see patients?" page.

FIG. 4I is an exemplary "Where do your providers see patients?" page. Three checkboxes are presented to the user (in this example, Office, Hospital and Other). In some examples, other checkboxes are presented to the user (e.g., Out Patient Facility, Home). Depending on answers provided by the user, the user is navigated to specific pages.

For example, if the user selects Office only, go to an Office name page, as illustrated by FIG. 4J, then an office address page (FIG. 4K). If user clicks Yes to the "Do you have another office?" prompt on the office address page, the user is navigated back to the office name page again to enter the new office. If user selects No on the office address page, the user is navigated to the Summary page, as illustrated by FIG. 4Q. If user selects Hospital only, the user is navigated to a hospital name page, as illustrated by FIG. 4L, and then to a hospital address page, as illustrated by FIG. 4M. If user selects Yes to add another hospital on the hospital address page, the user is navigated back to the hospital name page. If user selects No, the user is navigated to the department summary page, as illustrated by FIG. 4Q.

If the user selects Other only, the user is navigated to the "enter additional place of service" page, as illustrated by FIG. 4N, and then to an "enter 'place of service' name" page, as illustrated by FIG. 4O. The enter place of service name page typically indicates the first "place of service" type name chosen on for the "enter additional place of service" page. After the "enter place of service name" page, the user is navigated to the enter place of service address page, as illustrated by FIG. 4P. If user selects Yes to enter another place of service type, on the "enter place of service address" page, the user is navigated back to the "enter additional places of service" page. Typically the user will be navigated back with same place of service type name inserted in first sentence and the name fields are blank. If user selects No and the user chose more than one place of service type on the enter additional places of service page, the user is navigated to next place of service type name inserted in first sentence and name fields are left blank. If user selects No and he did not choose more than one place of service type on the "Where do your providers see patients" page, the user is navigated to the summary page, as illustrated by FIG. 4Q. If the user selects a combination of the above, the user is navigated through the pages in order with office first and place of service last.

FIG. 4O depicts one implementation of the "Enter 'Place of Service' (POS) name" page. As part of the display, the POS type chosen on the "Enter additional places of service" page is displayed. In some examples, a link "Oops, I picked the wrong one" is included that navigates the user back to the "Enter additional places of service" page where user can deselect the POS type. If the user deselects POS type and has already entered data for each POS type selected, the continue button navigates the user to the summary page. If user deselects POS type, but has not entered data for each POS type selected, the continue button navigates the user to the "Enter POS Name" page.

FIG. 4Q depicts a summary page for the departments section. In some examples, each type of department has its own row, and the address, phone, and fax are repeated for each type. When the user clicks the "add department" link, a dialog box is displayed (FIG. 4R) asking "Which type of department would you like to add?" typically with radio button choices of office, hospital, or other.

In other examples, FIG. 4R includes buttons for Cancel and OK, with OK being the default choice if the user hits Enter. Office choice navigates the user to the enter office name page, as illustrated by FIG. 4J. Hospital choice navigates the user to the enter hospital name page, as illustrated by FIG. 3L. Other navigates the user to the "enter additional places of service" page, as illustrated by FIG. 3N. When the user finishes entering the new department, the continue button returns the user to the department summary page where the user can choose the "add department" link again if they need to.

Departments, like medical groups, also utilize business logic (validation rules) to determine if the entered data is valid. In some examples, department validation logic includes, for example: all name fields must be populated with letters (periods, commas, and dashes allowed), all address fields must be populated (free text field, no rules), all city, state, zip, and phone fields must be populated, fax fields are optional. Additional rules include, for example, on the enter hospital name page, as illustrated by FIG. 4L, at least one hospital type box must be checked. Such logic is typically performed using string comparison functions and/or any other logic operation.

In addition to the individual fields, validation can be, for example, run against the department data as a whole. For example, office, hospital, and place of service names cannot be duplicated. If no hospital is provided by the user at all, a warning is displayed that reads: "You indicated that your providers do not see patients in a hospital. If this is incorrect, make sure you use the add department link to add a hospital." If no office is provided, a warning is displayed that reads: "You indicated that your providers do not see patients in an office. If this is incorrect, make sure you use the add department link to add an office." If the user indicated that they had a certain POS, yet didn't enter any data for it, a warning is displayed that reads: "You indicated that you had the following place of service type: <insert type of POS>, but you have not entered any data about this facility. If you chose this place of service type by mistake, return to the 'Where do your providers see patients?' page and deselect this POS type. Otherwise, please click 'add another department;' choose 'Other;' and select the appropriate POS." In other examples, a practice must have at least one department for the practice entry to be valid. Results of the validation of the section are similar to those of the medical group with respect to error messages and rollover text (e.g., error messages and/or rollover text) includes, for example:

Displaying an error symbol next to a row in which data is missing or invalid, with rollover text reading: "<insert error>. Click the update link to correct problems."

Displaying an error symbol next to a row in which data is missing or invalid, rollover text reading: "You entered a hospital department, yet you did not choose a type of department for this hospital. Please correct this error."

Returning an error message below the summary data (with error symbol to left of message) stating: "You cannot have more than one department with the same name. Please correct this error."

Returning an error message below the summary data (with error symbol to left of message) stating: "Your practice must have at least one department. Please enter a department."

In some examples, there is a section to configure providers for the medical practice, depicted in FIG. 4S. Beneficially, if the user already provided the information for a provider as a medical group (e.g., a single practitioner) the tool can re-use the original information and/or configure the medical practice to use the medical group information for that provider without additional information. For example, in some versions, if a social security number was provided to the tool when configuring the provider, the following text is displayed below last paragraph (of FIG. 4S) "Remember, you already entered <b><Dr. Last Name></b> during medical group setup. You <b>do not</b> need to enter him as a provider because he has already been entered." where <Dr. Last Name> is substituted with "Dr." and the last name of the person that matches the already provided social security number.

FIG. 4T depicts an exemplary "enter provider" page for entering information about a provider. If a provider was already entered in the medical group section, the First Name through Degree fields are pre-populated with that provider's information. If the provider was not already entered during the medical group section, the fields are presented as blank fields. Once the user has completed the First name, Last name and Degree fields, clicking Yes will save the data and clear the fields so the user can enter another provider. If the user is done, the user, upon clicking No, is navigated to the Signatures on File page, illustrated by FIG. 4U.

If the user has not completed those fields, clicking No navigates the user to the summary page for providers, illustrated by FIG. 4V. When that happens, a warning appears on the summary page for providers next to the row due to missing fields. In some implementations, the degree drop down includes the following options: MD, Doctor of Osteopathy (DO), Nurse Practitioner (NP), Physician's Assistant (PA), Medical Assistant (MA), Registered Nurse (RN), Licensed Practical Nurse (LPN), Resident, Locum Tenens, Certified Nurse Midwife (CNM), Perinatal Coordinator (PNC), Nutritionist (NUTR), Physical Therapist (OTR), Licensed Physical Therapist (LPT), Licensed Physical Therapy Assistant, Doctor of Podiatric Medicine, Doctor of Chiropractic, Certified Clinical Audiologist, Certified First Assistant, Certified Surgical Technician, MS/RD, Clinical Psychologist (EDD), Clinical Psychologist (PHD), Social Worker, Master Social Worker (MSW), Licensed Social Worker (LCSW), Licensed Professional Counselor (LPC), and/or Optometrist (OD).

In other examples, the medical group membership drop down menu includes all medical groups entered in medical group section. Generally, the specialty drop down menu includes various specialties (e.g., internal medicine, family practice). Beneficially, the tool can populate the specialty dropdown and the taxonomy look-up with specialties and taxonomical information stored in the databases of the medical practice management server. If necessary, upon navigating to the provider summary page, illustrated by FIG. 4V, the user can click "add provider link" to get back into provider workflow.

FIG. 4U is an exemplary "signatures on file" page: Typically the signatures on file page displays all the providers who have been entered (First name, Middle initial, Last name, degree) with check boxes next to the respective provider's names. The checkboxes should generally all be checked for the page to pass the validation business logic. Advantageously, the "signatures on file" page ensures that a medical practice is complying with HIPAA regulations that every provider have a signature on file with the medical practice where they provide services.

FIG. 4V depicts one implementation of a summary of provider information page. Like the medical group and the department sections, the summary of provider information page executes validation business logic to determine if the values provided in each field during configuration were valid. In some examples, validation includes first name and last name fields must be populated with letters (periods, commas, single quotes and dashes allowed), all fields except middle name and suffix must have values to pass, and/or each provider should have signature on file checked. Additionally, the section as a whole has validation business logic. For example, combinations of provider first name and last name cannot be duplicated and the practice must have at least one provider.

If the field values fail the validation, an error symbol is displayed next to the row in which data is missing or invalid. Rollover text is presented that reads, "<insert error>. Click the update link to correct problems." If there is no signature on file for a provider, a warning symbol next to appropriate row is displayed, with rollover text reading, "You indicated that you do not have a signature on file for this provider. If this is true, the medical practice management system will not be able to submit claims on his or her behalf." If multiple providers have the same combination of first name and last name, an error is displayed, stating "You cannot have more than one provider with the same name. Please correct this error by updating the proper entries." If no provider is provided, an error message is displayed stating, "Your practice must have at least one provider. Please enter a provider."

FIG. 4W depicts one implementation of an "end of practice chapter" page. Beneficially the "end of practice chapter" page provides links to each of the sections. If errors still exist within a section, a graphic appears next to the link for that section to alert the user that there is still an error. Advantageously, the user may return to a given section to add, update, delete, etc., data in that section, but the user does not have to go through the entire medical practice management system set up again.

In some examples, different messages are displayed on the end of practice chapter page depending on if errors exist with the sections or not. If no errors and no warnings in any of the sections, typically a message such as, "if you would like to review your work before proceeding, use the links below." If at least one error and no warnings the message "the <insert section name> section contains errors. Click the <insert section name> link to return to Summary page and fix errors," is displayed.

If the user is done, the user clicks the "I'm done" button and validation business logic is performed on the entire practice chapter. If the values and sections pass the validation business logic, the user is navigated to the review of practice chapter page, illustrated by FIG. 4X, and the user is done.

If, however, there are errors in some of the fields, the user is navigated to a review of practice chapter page that displays an error message, illustrated by FIG. 4Y. When an error still exists, a link is provided to section summary page that contains the errors. The user typically must fix all errors before he can proceed. Once the last error is fixed, success or warning message appear.

Lastly, if no errors exist, but the system has provided warnings, the user is navigated to review of practice chapter page that displays the warnings along with links to the appropriate sections, illustrated by FIG. 4Z. Warnings are the typically the same as section summary warnings, but include some context. For example, warnings should be prefaced with, "In the Provider section, <insert warning>". This review of practice chapter page allows a user to accept the warnings by providing an OK button. If the user clicks on the OK button, the user has acknowledged that they have seen the warnings and do not need to fix the potential configuration issues. However, if user goes back to a section that has a warning and does something that should generate a new warning, that new warning should appear next time user gets to the Chapter review audit.

Beneficially, the information provided during the setup allows the tool to configure the medical practice management server to be utilized by the practice. Similar features are provided for setting up payors (e.g., providing payor addresses and claim submission information) patients, operations, financials, and/or training.

In some examples, rather than guiding the user through a series of screens for a particular question area, data upload capability is provided. For example, in one version a user is presented with an input to upload a provider database or spreadsheet ("upload data"). The upload data includes information associated with a medical services provider (e.g., a doctor's name, address, and billing identifier). The user provides the upload data, and the interface is changed in response. In some examples, the response is an acknowledgement that the upload data was uploaded successfully. In other examples, the upload data is examined and values are stored in a data repository (e.g., inserted into a database table(s)) representing values in the upload data, relationships between values in the upload data, or both. For example, if Doctor Smith and Doctor Doe are providers associated with the medical practice, and both work at the same location, in one example, the address for each is stored in a data repository, as is the relationship that each is associated with that address. In some examples, the user is then prompted to accept the relationship.

In some examples, during configuration, the tool stores the input received from the user, preferably in a temporary database. In these examples, if a user exits the automated configuration, or returns to an earlier portion of the configuration, the system displays the previously received input when the user returns to a screen where the user has already provided input. For example, using the example above, after the user has provided that the medical practice is not associated with a mid-wife, assume the user exits the configuration program before completing the configuration. When the user begins the automated configuration tool again, the non-association with the midwife is retrieved and requires no further input from the user. The tool then provides the next set of screens (e.g., does the medical practice provide pre-natal education classes). This is beneficial in that if a user is forced to exit (e.g., for computer system maintenance) the user typically does not have to re-enter information, thus saving time spent configuring the system. In some examples where temporary tables are used, data is copied into non-temporary database tables at periodic time intervals, after the completion of the automated configuration tool, or both.

In some examples, as the user provides input, the tool configures the medical practice management system. Continuing the previous example, because the medical practice is not associated with a mid-wife, the tool does not create data structures (e.g., database tables, columns) for entering midwife information. But because the medical practice provides pre-natal education classes, data structures associated with that service are created.

Additionally or alternatively, based on the configuration information provided, in some examples, workflow rules are created for use by the workflow processing module. For example, as a patient in checking or checking out, the medical practice management system determines the reason for the patient's visit. Because the patient's visit to the medical practice is associated with an early pregnancy check up, the medical practice management system, and because the medical practice offers pre-natal classes, the medical practice management server prompts the user of the medical practice module to inform the patient about the pre-natal classes.

Figure 5:
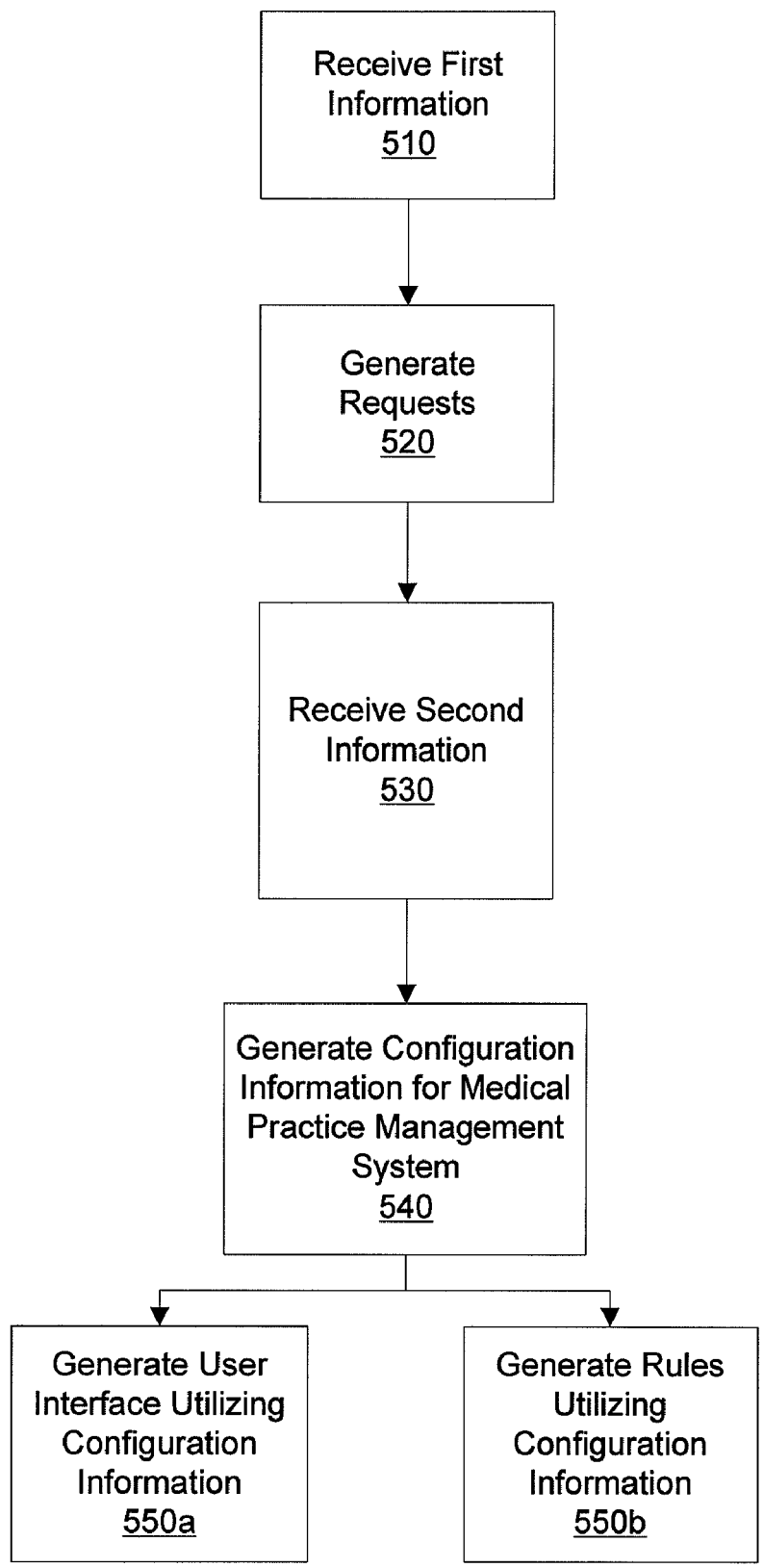
FIG. 5 is an exemplary flowchart depicting generating configuration information.

FIG. 5 is an exemplary flowchart 500 depicting generating configuration information utilizing the medical practice management system 100 of FIG. 1. The server configuration module 155 receives (510) first information that is communicated by the user 110 through the medical practice module 120. The server configuration module 155 generates (520) requests for additional information from the user 110. The server configuration module 155 receives (530) second information that is communicated by the user 110 through the medical practice module 120 in response to the requests for additional information. The server configuration module 155 generates (540) configuration information for the medical practice to utilize the medical practice management system 100. The server configuration module 155 generates (550a and 550b) a user interface to the medical practice management system 100 and rules for medical practice management system 100, respectively, based on the configuration information.

For example, a medical office manager 110 utilizes the medical practice configuration module 125 (e.g., configuration user interface) on the medical practice module 120 to input the medical office's address (in this example, 123 Main Street West City, N.J.), doctor information (e.g., name of doctors in the practice, degree of each doctor), and the insurance company identification (i.e., the insurance companies and plans that are accepted by the medical office). The server configuration module 155 receives (510) the information about the medical practice. The server configuration module 155 generates (520) requests for additional information based on the information and on rules associated with the identified insurance companies and plans that are accepted by the medical office. The medical office had indicated that it accepts the premium high insurance plan from insurance company Medical Omega. Based on a rule stored in the payor information database 175 from the premium high insurance plan at Medical Omega which indicates that the insurance company requires a specialist associated with the specific type of medical encounter approve the medical encounter if the cost exceeds $1,000, the server configuration module 155 generates (520) a request to find out the specialty of each doctor in the medical practice.

The medical office manager 110 responds to the request with additional information and the server configuration module 155 receives (530) the additional information (in this example, the specialty of each doctor in the medical practice). The server configuration module 144 generates (540) configuration information based on the information received from the medical practice. The configuration information includes the specialty of each doctor in the medical practice so that the information can be submitted with insurance claims for the premium high insurance plan from insurance company Medical Omega.

The server configuration module 155 generates (550a) a user interface (e.g., a plurality of web pages for use by the medical practice) for use by the medical practice. The user interface includes fields that indicate the specialty for each doctor, so that the user can associated medical encounters with doctor approvals. The server configuration module 155 generates (550b) a rule for the medical practice that when a new doctor is added to the medical practice management system 100 then the specialty of the doctor, if the doctor has a specialty, has to be entered into the system 100.

In some examples, the configuration information is utilized to generate a data structure for the medical practice. The data structure can include, for example, data fields, tables, and/or rows for the database. The data structure can be stored, for example, in the medical practice information database 165. For example, if the medical office includes an oral surgeon who does in-patient surgeries (e.g., wisdom teeth removal), then data structures can be created to include the information needed for in-patient surgeries in the medical office.

In other examples, the requests generated (520) for additional information are based on one or more insurance rules that apply to the payor servers that are associated with the medical office. The payor servers are associated with the medical office based on the information inputted by the user 110 about the medical office. The one or more insurance rules can be stored, for example, in the payor information database 175 and can be accessed, for example, through the payor module 170. The payor module 170 can update, for example, the insurance rules based on information received from the payor servers (not shown).

In some examples, the configuration information includes information that selects information for submission to a payor server (e.g., doctor's medical degree information). The configuration information can include, for example, information that formats information for submission to a payor server (e.g., doctor's medical degree has to be in the format M.D. or O.D.).

In other examples, the configuration tool can be utilized to update information for a medical practice. The information about a medical practice may need to be updated based changes to the medical practice (e.g., addition of new medical office, new doctor, new insurance plan). The updated configuration information that is generated based on the new information can be merged, for example, into the existing configuration information (e.g., adding new data structure for the new medical office). In some examples, the new configuration information replaces the existing configuration information in the medical practice information database 165.

Figure 6:
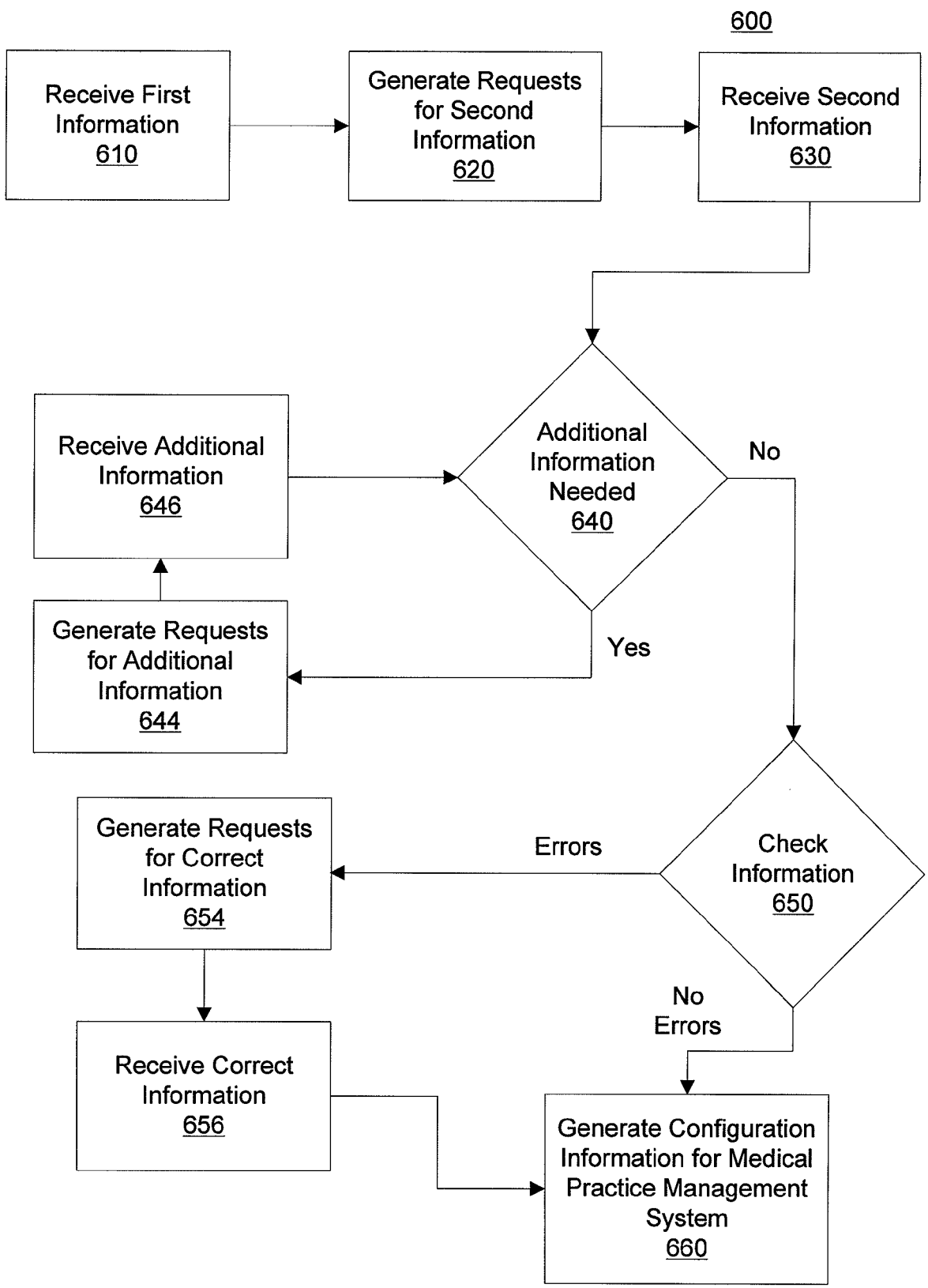
FIG. 6 is an exemplary flowchart depicting determining if additional information is needed and determining if the information is correct.

FIG. 6 is an exemplary flowchart 600 depicting determining if additional information is needed and determining if the information is correct utilizing the medical practice management system 100 of FIG. 1. The medical practice module 120 receives (610) first information that is communicated by the user 110. The server configuration module 155 generates (620) requests for additional information from the user 110. The medical practice module 120 receives (630) second information that is communicated by the user 110 in response to the requests for additional information.

The server configuration module 155 determines (640) whether additional information is needed for the configuration of the medical practice. The determination (640) of whether additional information is needed includes processing one or more rules associated with payor servers which are associated with the medical practice based on the information submitted by the user 110. If additional information is needed, then the server configuration module 155 generates (644) requests for additional information. The user 110 receives the requests for additional information and submits additional information in response to the requests. The medical practice module 120 receives (646) the additional information. The server configuration module 155 then determines (640) again whether additional information is needed for the configuration of the medical practice.

If no additional information is needed, then the server configuration module 155 checks (650) all of the received information for errors (e.g., missing information, incorrect information). If there are errors in the received information, then the server configuration module 155 generates (654) requests for correct information. The user 110 receives the requests for additional information and submits updated information to the server configuration module 155. The medical practice module 120 receives (656) the correct information.

If there are no errors in the received information or the errors have been corrected, the server configuration module 155 generates (660) configuration information for the medical practice to utilize the medical practice management system 100.

In some examples, the errors include incorrect information, missing information, and/or any other issue with the information. The configuration information can include, for example, medical claim processing information, user interface information, data structure information, rule information, and/or any other type of medical office configuration information. The errors can be, for example, automatically corrected by the system 100 based on information associated with the medical practice and/or rules associated with the medical practice.

In some examples, the medical practice module (e.g., 125, 220*a*, 220*b*) can be any computing device, personal computer, Windows-based terminal, network computer, wireless device, information appliance, RISC Power PC, X-device, workstation, mini computer, main frame computer, personal digital assistant, and/or other computing device that has a windows-based desktop. In other examples, the medical practice module (e.g., 125, 220*a*, 200*b*) can connect to a network and has sufficient persistent storage for executing a small, display presentation program (e.g., Java applet, CGI enable web page). Windows-oriented platforms supported by the medical practice module (e.g., 125, 220*a*, 220*b*) can include, for example and without limitation, Windows 3.X, Windows 95, Windows 98, Windows NT 3.51, Windows NT 4.0, Windows 2000, Windows XP, Windows Vista, Windows CE, Windows Mobile, Mac/OS, OS X, Java, Unix, and/or Linux. The medical practice module can include, for example, a visual display device (e.g., a computer monitor), a data entry device (e.g., a keyboard), persistent or volatile storage (e.g., computer memory) for storing downloaded application programs, a processor, and/or a pointing device such as a mouse or digitized pen.

In other examples, the medical practice module includes a medical practice client user interface. The medical practice client interface can be, for example, text driven (e.g., DOS) and/or graphically driven (e.g., Windows). In some examples, the medical practice client user interface is a web browser, such as Internet Explorer™ developed by Microsoft Corporation (Redmond, Wash.), to connect to the medical practice management server. In other examples, the web browser uses the existing Secure Socket Layer (SSL) support, developed by Netscape Corporation, (Mountain View, Calif.) to establish the medical practice network as a secure network.

In some examples, the medical practice management server and/or the payor server can be any personal computer. In another example, the medical practice management server hosts one or more applications that the medical practice module can access (e.g., employee time entry, medical database). The medical practice management server can be, for example, part and/or associated with a server farm (e.g., a logical group of one or more servers that are administered as a single entity).

The above-described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device and/or in a propagated signal, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

The components of the system can be interconnected by any form or medium of digital data communication (e.g., a communication network). Examples of communication networks include a LAN, WAN, the Internet, wired networks, and/or wireless networks.

The networks can be, for example, a wireless network and/or a wired network. The networks can be, for example, a packet-based network and/or a circuit-based network. Packet-based networks can include, for example, the Internet, a carrier internet protocol (IP) network (e.g., LAN, WAN, campus area network (CAN), MAN, home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The computing device can include, for example, a computer, a computer with a browser device, a telephone, an IP phone, a mobile computing device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). The mobile computing device includes, for example, a personal digital assistant (PDA).

Doctor and physician are open ended and include any type of healthcare professional referred to as a doctor and/or a physician. Comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method for automated computerized configuration of a medical practice management system, the method comprising:

receiving, by a computerized medical practice management server, first information associated with a medical practice prior to configuring the medical practice to use the medical practice management system to process medical claims, wherein the first information includes information about the medical practice;

associating, by the computerized medical practice management server, one or more payor servers with the medical practice based on the first information;

generating, by the computerized medical practice management server, a request for second information that is required to configure the medical practice management system to process medical claims for patients of the medical practice, the request being based on (a) the first information and (b) one or more insurance rules stored in an insurance rules database that apply to one or more payor servers, wherein the one or more insurance rules apply to the one or more payor servers associated with the medical practice;

in response to the request, receiving, by the computerized medical practice management server, second information which comprises information indicative of requirements for submission of medical claims to the one or more payor servers;

generating, by the computerized medical practice management server, configuration information for the medical practice management system based on the first information and the second information, wherein the configuration information is used by the medical practice management server to ensure that medical claims transmitted from the medical practice satisfy the requirements of the one or more payor servers before the medical claims are transmitted to a payor server for payment; and configuring, by the computerized medical practice management server, the medical practice management system for use by one or more users at the medical practice based on the configuration information so that the medical practice management system can process medical claims transmitted from the one or more users at the medical practice.

2. The method of claim 1 further comprising dynamically generating a user interface for one or more users of the medical practice based on the configuration information, the user interface comprising one or more fields including information from the configuration information.

3. The method of claim 1 further comprising updating stored configuration information for the medical practice stored in a medical practice information database with the configuration information.

4. The method of claim 1 further comprising:
determining whether to request additional information based on the first information, the second information, and the one or more insurance rules;
generating a request for additional information based on the first information, the second information, and the one or more insurance rules;
receiving additional information, which comprises information indicative of requirements for submission of medical claims to the one or more payor servers, based on the request for additional information; and
generating configuration information for the medical practice management system based on the first information, the second information, and the additional information, wherein the configuration information is used by the medical practice management server to ensure that medical claims transmitted from the medical practice satisfy the requirements of the one or more payor servers before the medical claims are transmitted to a payor server for payment.

5. The method of claim 1 wherein the configuration information comprises medical claim processing information, medical claim information utilized to generate medical claims for submission to one or more payor server, or both, the method further comprising:
generating one or more rules for the medical practice management system based on the configuration information; and
storing the one or more rules in the insurance rules database.

6. The method of claim 1 further comprising:
determining one or more errors are associated with the first information, second information, or both based on one or more rules associated with one or more payor servers;
generating a request for correct information; and
receiving correct information based on the request for correct information.

7. The method of claim 1 further comprising selecting third information for submission to a payor server based on the configuration information.

8. The method of claim 7 further comprising formatting the third information for submission to the payor server based on the configuration information.

9. A computer program product, tangibly embodied in a machine readable storage device, the computer program product including instructions being operable to cause a data processing apparatus to:
receive first information associated with a medical practice prior to configuring the medical practice to use the medical practice management system to process medical claims, wherein the first information includes information about the medical practice;

associate one or more payor servers with the medical practice based on the first information;

generate a request for second information that is required to configure the medical practice management system to process medical claims for patients of the medical practice, the request being based on (a) the first information and (b) one or more insurance rules stored in an insurance rules database that apply to one or more payor servers, wherein the one or more insurance rules apply to the one or more payor servers associated with the medical practice;

in response to the request, receive second information which comprises information indicative of requirements for submission of medical claims to the one or more payor servers;

generate configuration information for the medical practice management system based on the first information and the second information, wherein the configuration information is used by the medical practice management server to ensure that medical claims transmitted from the medical practice satisfy the requirements of the one or more payor servers before the medical claims are transmitted to a payor server for payment; and configure the medical practice management system for use by one or more users at the medical practice based on the configuration information so that the medical practice management system can process medical claims transmitted from the one or more users at the medical practice.

10. An apparatus for automated computerized configuration of a medical practice management system, the system comprising:

a medical practice module configured to:

receive first information associated with a medical practice prior to configuring the medical practice to use the medical practice management system to process medical claims, wherein the first information includes information about the medical practice;

receive second information, which comprises information indicative of requirements for submission of medical claims to one or more payor servers, based on a request; and configure the medical practice management system for use by one or more users at the medical practice based on the configuration information so that the medical practice management system can process medical claims transmitted from the one or more users at the medical practice;

a server configuration module in communication with the medical practice module configured to:

associate one or more payor servers with the medical practice based on the first information;

generate the request for the second information that is required to configure the medical practice management system to process medical claims for patients of the medical practice, the request being based on (a) the first information and (b) one or more insurance rules that apply to the one or more payor servers, wherein the one or more insurance rules apply to the one or more payor servers associated with the medical practice; and generate configuration information for the medical practice management system based on the first information and the second information, wherein the configuration information is used by the medical practice management server to ensure that medical claims transmitted from the medical practice satisfy the requirements of the one or more payor servers before the medical claims are transmitted to a payor server for payment; and an insurance rules database in communication with the server configuration module configured to store the one or more insurance rules.

* * * * *